US009581603B2

(12) United States Patent
Vandroux et al.

(10) Patent No.: US 9,581,603 B2
(45) Date of Patent: Feb. 28, 2017

(54) COLLAGEN-DERIVED RECOMBINANT PROTEINS WITH VON WILLEBRAND FACTOR-BINDING ACTIVITY

(71) Applicants: NVH Medicinal, Dijon (FR); Centre Hospitalier Universitaire De Dijon, Dijon (FR)

(72) Inventors: David Vandroux, Dijon (FR); Emmanuel De Maistre, Fontaine-les-Dijon (FR); Francois Coutard, Ales (FR); Laure Dumont Di Leone, Dijon (FR)

(73) Assignees: NVH Medicinal (FR); Centre Hospitalier Universitaire De Dijon (FR)

( * ) Notice: Subject to any disclaimer, the term of this patent is extended or adjusted under 35 U.S.C. 154(b) by 0 days.

(21) Appl. No.: 14/436,628

(22) PCT Filed: Oct. 18, 2013

(86) PCT No.: PCT/EP2013/071816

§ 371 (c)(1),
(2) Date: Apr. 17, 2015

(87) PCT Pub. No.: WO2014/060568

PCT Pub. Date: Apr. 24, 2014

(65) Prior Publication Data

US 2015/0276762 A1 Oct. 1, 2015

(30) Foreign Application Priority Data

Oct. 19, 2012 (FR) ..................................... 12 59996

(51) Int. Cl.

| | |
|---|---|
| ***A61K 38/17*** | (2006.01) |
| ***C07K 1/00*** | (2006.01) |
| ***C07K 14/00*** | (2006.01) |
| ***C07K 16/00*** | (2006.01) |
| ***C07K 17/00*** | (2006.01) |
| ***G01N 33/68*** | (2006.01) |
| ***C07K 14/78*** | (2006.01) |

(52) U.S. Cl.

CPC ......... *G01N 33/6893* (2013.01); *C07K 14/78* (2013.01); *C07K 2319/02* (2013.01); *G01N 2333/745* (2013.01); *G01N 2333/78* (2013.01); *G01N 2800/222* (2013.01); *G01N 2800/224* (2013.01)

(58) Field of Classification Search

CPC ................ C07K 14/78; C07K 2319/02; G01N 2333/745; G01N 2333/78; G01N 2800/222; G01N 2800/224; G01N 33/6893

See application file for complete search history.

(56) References Cited

U.S. PATENT DOCUMENTS

| | | | | |
|---|---|---|---|---|
| 8,163,496 B2 * | 4/2012 | Montgomery | ..... G01N 33/5008 | 435/13 |
| 8,318,444 B2 * | 11/2012 | Montgomery | ..... G01N 33/5008 | 435/7.1 |
| 8,865,415 B2 * | 10/2014 | Montgomery | ..... G01N 33/5008 | 435/7.1 |
| 9,046,535 B2 * | 6/2015 | Montgomery | ..... G01N 33/5008 | |
| 2007/0099244 A1 * | 5/2007 | Xu | ......................... C07K 14/78 | 435/7.2 |
| 2012/0116053 A1 * | 5/2012 | Mirochnitchenko | .. C07K 14/78 | 530/350 |

FOREIGN PATENT DOCUMENTS

| | | | | |
|---|---|---|---|---|
| EP | 1870460 A1 | 12/2007 | | |
| EP | 2383338 A1 | 11/2011 | | |
| WO | 2007052067 A2 | 5/2007 | | |
| WO | WO2009009493 | * | 1/2009 | ........... C07K 13/435 |
| WO | WO2010091251 | * | 2/2010 | |
| WO | 2010034718 A1 | 4/2010 | | |

OTHER PUBLICATIONS

International Search Report issued from corresponding PCT/EP2013/071816, dated Nov. 27, 2013.
Baronciani L et colt. J Thromb Haemost. Sep. 2006;4(9):2088-90.
Bonnefoy et colt. J ThrombHaemost. Oct. 2006;4(10):2151-61.
Brondijk TH et coLt. ProcNattAcadSci U S A. Apr. 3, 2012;109(14):5253-8.
Chen C, et al., "Focus on collagen: in vitro systems to study firbogenesis and antifibrosis—state of the art," Fibrogenesis Tissue Repair, Dec. 15, 2009, 10 pages.
Chen J et coLt., J Clin Invest.2011 121(2) :593-603.
Favaloro EJ, Thromb Haemost. Nov. 2010; 104(5): 1009-21.
Flood VH, et al, "Comparison of type I, type III and type VI colagen binding assays in diagnosis of von Willebrand disease," J Thromb Haemost, Apr. 16, 2012, 10: 1425-1432.
Giudici Cet colL., J Blot Chem. Jul. 11, 2008;283(28):19551-60.
Heemskerk JWM et colt. J Thromb Haemost. Apr. 2011;9(4):856-8.
Herr, AB, et al., "Structural Insights into the Interactions between Platelet Receptors and Fibrillar Collagen," J Bio Chem, Jul. 24, 2009, 384(30), pp. 19781-19785.
Lisman, T, et al. "A single high-affinity binding site for von Willebrand factor in collagen III, identified using sythentic triple-helical peptides," Blood, Dec. 1, 2006, 108(12), pp. 3753-3756.
Neddleman et Wunsch, J MolBiol 1970 48:443.
Schneppenheim R, "The pathophysiology of von Willbrand disease: therapeutic implications," Thromb Research, 2011; 128 Suppl, pp. S3-S7.
Springer TA, "Biology and physics of van Willebrand factor concatamers," J Thromb Haemost, Jul. 9, 2011, (Suppl 1): 30-43.
Verkteijet colt, BLood. May 15, 1998; 91(10): 3808-16.
Werkmeister J etRamshaw J. Biomed Mater. Feb. 2012;7(1):01 2002.
Xu H, et al, "Collagen binding specificity of the discoidin doimain receptors: Binding sites on collagens II and III and molecular determinants for collagen IV recognitiion by DDR1," Matrix Biology, Jan. 2011, 30(1), pp. 16-26.
Pugh Nicholas et al., Blood, vol. 115, No. 24, Jun. 2010.

* cited by examiner

*Primary Examiner* — Marcela M Cordero Garcia
(74) *Attorney, Agent, or Firm* — Banner & Witcoff, Ltd.

(57) ABSTRACT

A method for diagnosing von Willebrand disease and novel polypeptides which bind to von Willebrand factor.

9 Claims, 6 Drawing Sheets

Figure 1:
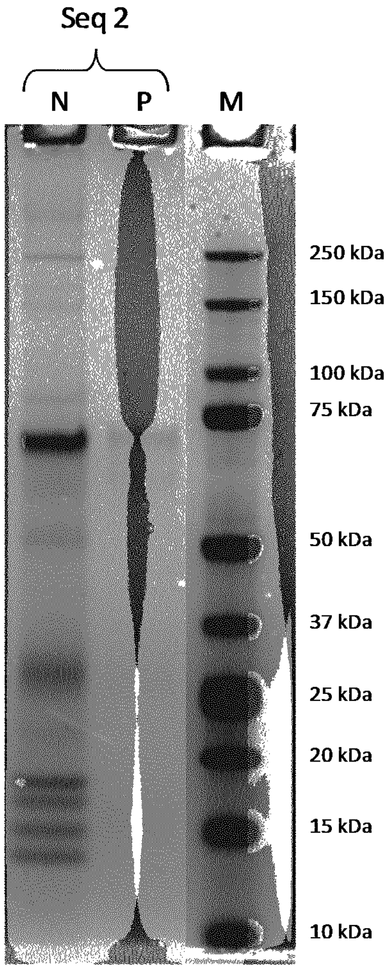

SEQUENCE LISTING

```
<160> NUMBER OF SEQ ID NOS: 17

<210> SEQ ID NO 1
<211> LENGTH: 552
<212> TYPE: DNA
<213> ORGANISM: Artificial
<220> FEATURE:
<223> OTHER INFORMATION: Polynucleotide encoding a polypeptide
      comprising two von Willebrand factor-binding motifs

<400> SEQUENCE: 1

atgatgagct tcgtgcagaa ggggagctgg ctgcttctcg ctctgcttca tcctactatt     60

atcctggcac aggggcgccc cggagctcct ggagagagag gattgcctgg acctccaggg    120

cccagaggag ctgctggaga acctggcaga gatggcgtcc ctggaggacc aggaatgagg    180
```

-continued

```
ggcatgcccg gaagcccagg aggaccagga agcgatggga agccagggcc tcccggaagc    240

cagggagaaa gcggcagacc aggacctcct ggagagaacg gattccctgg agaaaggggg    300

gatgcaggcg ctcctggggc accaggacct cgtggccagc ccggggtgat gggattcccc    360

ggggatgccg gggcacctgg tgcacctggc ccacgtgggc agcctggagt catggggttc    420

cctggaccac ctggcccacc aggccctccc ggaccacctg gacctccagg ccctcctggc    480

cctcctggac ctcctggacc acctggacct ccaggcccaa gaggcgacaa gggacctcct    540

ggacctggat ct                                                        552


<210> SEQ ID NO 2
<211> LENGTH: 184
<212> TYPE: PRT
<213> ORGANISM: Artificial
<220> FEATURE:
<223> OTHER INFORMATION: Polypeptide comprising two von Willebrand
      factor-binding motifs

<400> SEQUENCE: 2

Met Met Ser Phe Val Gln Lys Gly Ser Trp Leu Leu Leu Ala Leu Leu
1               5                   10                  15

His Pro Thr Ile Ile Leu Ala Gln Gly Arg Pro Gly Ala Pro Gly Glu
            20                  25                  30

Arg Gly Leu Pro Gly Pro Pro Gly Pro Arg Gly Ala Ala Gly Glu Pro
        35                  40                  45

Gly Arg Asp Gly Val Pro Gly Gly Pro Gly Met Arg Gly Met Pro Gly
    50                  55                  60

Ser Pro Gly Gly Pro Gly Ser Asp Gly Lys Pro Gly Pro Pro Gly Ser
65                  70                  75                  80

Gln Gly Glu Ser Gly Arg Pro Gly Pro Pro Gly Glu Asn Gly Phe Pro
                85                  90                  95

Gly Glu Arg Gly Asp Ala Gly Ala Pro Gly Ala Pro Gly Pro Arg Gly
            100                 105                 110

Gln Pro Gly Val Met Gly Phe Pro Gly Asp Ala Gly Ala Pro Gly Ala
        115                 120                 125

Pro Gly Pro Arg Gly Gln Pro Gly Val Met Gly Phe Pro Gly Pro Pro
    130                 135                 140

Gly Pro Pro Gly Pro Pro Gly Pro Pro Gly Pro Pro Gly Pro Pro Gly
145                 150                 155                 160

Pro Pro Gly Pro Pro Gly Pro Pro Gly Pro Pro Gly Pro Arg Gly Asp
                165                 170                 175

Lys Gly Pro Pro Gly Pro Gly Ser
            180


<210> SEQ ID NO 3
<211> LENGTH: 163
<212> TYPE: PRT
<213> ORGANISM: Artificial
<220> FEATURE:
<223> OTHER INFORMATION: Polypeptide comprising one von Willebrand
      factor-binding motif

<400> SEQUENCE: 3

Met Met Ser Phe Val Gln Lys Gly Ser Trp Leu Leu Leu Ala Leu Leu
1               5                   10                  15

His Pro Thr Ile Ile Leu Ala Gln Gly Arg Pro Gly Ala Pro Gly Glu
            20                  25                  30
```

```
Arg Gly Leu Pro Gly Pro Pro Gly Pro Arg Gly Ala Ala Gly Glu Pro
        35                  40                  45

Gly Arg Asp Gly Val Pro Gly Gly Pro Gly Met Arg Gly Met Pro Gly
    50                  55                  60

Ser Pro Gly Gly Pro Gly Ser Asp Gly Lys Pro Gly Pro Pro Gly Ser
65                  70                  75                  80

Gln Gly Glu Ser Gly Arg Pro Gly Pro Pro Gly Glu Asn Gly Phe Pro
                85                  90                  95

Gly Glu Arg Gly Asp Ala Gly Ala Pro Gly Ala Pro Gly Pro Arg Gly
            100                 105                 110

Gln Pro Gly Val Met Gly Phe Pro Gly Pro Pro Gly Pro Pro Gly Pro
        115                 120                 125

Pro Gly Pro Pro Gly Pro Pro Gly Pro Pro Gly Pro Pro Gly Pro Pro
    130                 135                 140

Gly Pro Pro Gly Pro Pro Gly Pro Arg Gly Asp Lys Gly Pro Pro Gly
145                 150                 155                 160

Pro Gly Ser


<210> SEQ ID NO 4
<211> LENGTH: 205
<212> TYPE: PRT
<213> ORGANISM: Artificial
<220> FEATURE:
<223> OTHER INFORMATION: Polypeptide comprising three von Willebrand
      factor-binding motifs

<400> SEQUENCE: 4

Met Met Ser Phe Val Gln Lys Gly Ser Trp Leu Leu Leu Ala Leu Leu
1               5                   10                  15

His Pro Thr Ile Ile Leu Ala Gln Gly Arg Pro Gly Ala Pro Gly Glu
            20                  25                  30

Arg Gly Leu Pro Gly Pro Pro Gly Pro Arg Gly Ala Ala Gly Glu Pro
        35                  40                  45

Gly Arg Asp Gly Val Pro Gly Gly Pro Gly Met Arg Gly Met Pro Gly
    50                  55                  60

Ser Pro Gly Gly Pro Gly Ser Asp Gly Lys Pro Gly Pro Pro Gly Ser
65                  70                  75                  80

Gln Gly Glu Ser Gly Arg Pro Gly Pro Pro Gly Glu Asn Gly Phe Pro
                85                  90                  95

Gly Glu Arg Gly Asp Ala Gly Ala Pro Gly Ala Pro Gly Pro Arg Gly
            100                 105                 110

Gln Pro Gly Val Met Gly Phe Pro Gly Asp Ala Gly Ala Pro Gly Ala
        115                 120                 125

Pro Gly Pro Arg Gly Gln Pro Gly Val Met Gly Phe Pro Gly Asp Ala
    130                 135                 140

Gly Ala Pro Gly Ala Pro Gly Pro Arg Gly Gln Pro Gly Val Met Gly
145                 150                 155                 160

Phe Pro Gly Pro Pro Gly Pro Pro Gly Pro Pro Gly Pro Pro Gly Pro
                165                 170                 175

Pro Gly Pro Pro Gly Pro Pro Gly Pro Pro Gly Pro Pro Gly Pro Pro
            180                 185                 190

Gly Pro Arg Gly Asp Lys Gly Pro Pro Gly Pro Gly Ser
        195                 200                 205


<210> SEQ ID NO 5
<211> LENGTH: 226
```

-continued

<212> TYPE: PRT
<213> ORGANISM: Artificial
<220> FEATURE:
<223> OTHER INFORMATION: Polypeptide comprising four von Willebrand factor-binding motifs

<400> SEQUENCE: 5

```
Met Met Ser Phe Val Gln Lys Gly Ser Trp Leu Leu Leu Ala Leu Leu
1               5                   10                  15

His Pro Thr Ile Ile Leu Ala Gln Gly Arg Pro Gly Ala Pro Gly Glu
            20                  25                  30

Arg Gly Leu Pro Gly Pro Pro Gly Pro Arg Gly Ala Ala Gly Glu Pro
        35                  40                  45

Gly Arg Asp Gly Val Pro Gly Gly Pro Gly Met Arg Gly Met Pro Gly
    50                  55                  60

Ser Pro Gly Gly Pro Gly Ser Asp Gly Lys Pro Gly Pro Pro Gly Ser
65                  70                  75                  80

Gln Gly Glu Ser Gly Arg Pro Gly Pro Pro Gly Glu Asn Gly Phe Pro
                85                  90                  95

Gly Glu Arg Gly Asp Ala Gly Ala Pro Gly Ala Pro Gly Pro Arg Gly
            100                 105                 110

Gln Pro Gly Val Met Gly Phe Pro Gly Asp Ala Gly Ala Pro Gly Ala
        115                 120                 125

Pro Gly Pro Arg Gly Gln Pro Gly Val Met Gly Phe Pro Gly Asp Ala
    130                 135                 140

Gly Ala Pro Gly Ala Pro Gly Pro Arg Gly Gln Pro Gly Val Met Gly
145                 150                 155                 160

Phe Pro Gly Asp Ala Gly Ala Pro Gly Ala Pro Gly Pro Arg Gly Gln
                165                 170                 175

Pro Gly Val Met Gly Phe Pro Gly Pro Pro Gly Pro Pro Gly Pro Pro
            180                 185                 190

Gly Pro Pro Gly Pro Pro Gly Pro Pro Gly Pro Pro Gly Pro Pro Gly
        195                 200                 205

Pro Pro Gly Pro Pro Gly Pro Arg Gly Asp Lys Gly Pro Pro Gly Pro
    210                 215                 220

Gly Ser
225
```

<210> SEQ ID NO 6
<211> LENGTH: 12
<212> TYPE: PRT
<213> ORGANISM: Artificial
<220> FEATURE:
<223> OTHER INFORMATION: Von Willebrand factor-binding motif

<400> SEQUENCE: 6

```
Gly Pro Arg Gly Gln Pro Gly Val Met Gly Phe Pro
1               5                   10
```

<210> SEQ ID NO 7
<211> LENGTH: 9
<212> TYPE: PRT
<213> ORGANISM: Artificial
<220> FEATURE:
<223> OTHER INFORMATION: Linker

<400> SEQUENCE: 7

```
Gly Asp Ala Gly Ala Pro Gly Ala Pro
1               5
```

<210> SEQ ID NO 8
<211> LENGTH: 42
<212> TYPE: PRT
<213> ORGANISM: Artificial
<220> FEATURE:
<223> OTHER INFORMATION: Linker-Von Willebrand factor-binding motif-Linker-Von Willebrand factor-binding motif

<400> SEQUENCE: 8

```
Gly Asp Ala Gly Ala Pro Gly Ala Pro Gly Pro Arg Gly Gln Pro Gly
1               5                   10                  15

Val Met Gly Phe Pro Gly Asp Ala Gly Ala Pro Gly Ala Pro Gly Pro
            20                  25                  30

Arg Gly Gln Pro Gly Val Met Gly Phe Pro
        35                  40
```

<210> SEQ ID NO 9
<211> LENGTH: 184
<212> TYPE: PRT
<213> ORGANISM: Artificial
<220> FEATURE:
<223> OTHER INFORMATION: Polypeptide comprising two von Willebrand factor-binding motifs encoded from the polynucleotide of SEQ ID NO:1

<400> SEQUENCE: 9

```
Met Met Ser Phe Val Gln Lys Gly Ser Trp Leu Leu Leu Ala Leu Leu
1               5                   10                  15

His Pro Thr Ile Ile Leu Ala Gln Gly Arg Pro Gly Ala Pro Gly Glu
            20                  25                  30

Arg Gly Leu Pro Gly Pro Pro Gly Pro Arg Gly Ala Ala Gly Glu Pro
        35                  40                  45

Gly Arg Asp Gly Val Pro Gly Gly Pro Gly Met Arg Gly Met Pro Gly
    50                  55                  60

Ser Pro Gly Gly Pro Gly Ser Asp Gly Lys Pro Gly Pro Pro Gly Ser
65                  70                  75                  80

Gln Gly Glu Ser Gly Arg Pro Gly Pro Pro Gly Glu Asn Gly Phe Pro
                85                  90                  95

Gly Glu Arg Gly Asp Ala Gly Ala Pro Gly Ala Pro Gly Pro Arg Gly
            100                 105                 110

Gln Pro Gly Val Met Gly Phe Pro Gly Asp Ala Gly Ala Pro Gly Ala
        115                 120                 125

Pro Gly Pro Arg Gly Gln Pro Gly Val Met Gly Phe Pro Gly Pro Pro
    130                 135                 140

Gly Pro Pro Gly Pro Pro Gly Pro Pro Gly Pro Pro Gly Pro Pro Gly
145                 150                 155                 160

Pro Pro Gly Pro Pro Gly Pro Pro Gly Pro Pro Gly Pro Arg Gly Asp
                165                 170                 175

Lys Gly Pro Pro Gly Pro Gly Ser
            180
```

<210> SEQ ID NO 10
<211> LENGTH: 12
<212> TYPE: PRT
<213> ORGANISM: Artificial
<220> FEATURE:
<223> OTHER INFORMATION: von Willebrand factor A3 domain_pro at position 6,12 is Hydroxyproline

<400> SEQUENCE: 10

Gly Pro Arg Gly Gln Pro Gly Val Met Gly Phe Pro
1 5 10

<210> SEQ ID NO 11
<211> LENGTH: 8
<212> TYPE: PRT
<213> ORGANISM: Artificial
<220> FEATURE:
<223> OTHER INFORMATION: alpha 1 chain motif

<400> SEQUENCE: 11

Arg Gly Gln Ala Gly Val Met Phe
1 5

<210> SEQ ID NO 12
<211> LENGTH: 9
<212> TYPE: PRT
<213> ORGANISM: Artificial
<220> FEATURE:
<223> OTHER INFORMATION: alpha 2 chain motif_pro at position 4 is Hydroxyproline

<400> SEQUENCE: 12

Arg Gly Glu Pro Gly Asn Ile Gly Phe
1 5

<210> SEQ ID NO 13
<211> LENGTH: 6
<212> TYPE: PRT
<213> ORGANISM: Artificial
<220> FEATURE:
<223> OTHER INFORMATION: integrin binding motif_pro at position 3 is Hydroxyproline

<400> SEQUENCE: 13

Gly Met Pro Gly Glu Arg
1 5

<210> SEQ ID NO 14
<211> LENGTH: 12
<212> TYPE: PRT
<213> ORGANISM: Artificial
<220> FEATURE:
<223> OTHER INFORMATION: linker_GXX repeat_Xaa at positions 2-3, 5-6, 8-9, 11-12 can be Asp, Ala, or Pro and up to four of them may be absent
<220> FEATURE:
<221> NAME/KEY: misc_feature
<222> LOCATION: (2)..(3)
<223> OTHER INFORMATION: Xaa can be Asp, Ala, or Pro
<220> FEATURE:
<221> NAME/KEY: misc_feature
<222> LOCATION: (5)..(6)
<223> OTHER INFORMATION: Xaa can be Asp, Ala, or Pro
<220> FEATURE:
<221> NAME/KEY: misc_feature
<222> LOCATION: (8)..(9)
<223> OTHER INFORMATION: Xaa can be Asp, Ala, or Pro
<220> FEATURE:
<221> NAME/KEY: misc_feature
<222> LOCATION: (11)..(12)
<223> OTHER INFORMATION: Xaa can be Asp, Ala, or Pro

<400> SEQUENCE: 14

Gly Xaa Xaa Gly Xaa Xaa Gly Xaa Xaa Gly Xaa Xaa
1 5 10

<210> SEQ ID NO 15
<211> LENGTH: 45
<212> TYPE: PRT

-continued

```
<213> ORGANISM: Artificial
<220> FEATURE:
<223> OTHER INFORMATION: peptide motif GPP repeat_up to eleven of
      them may be absent

<400> SEQUENCE: 15

Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro Gly Pro
            20                  25                  30

Pro Gly Pro Pro Gly Pro Pro Gly Pro Pro Gly Pro Pro
        35                  40                  45


<210> SEQ ID NO 16
<211> LENGTH: 18
<212> TYPE: PRT
<213> ORGANISM: Artificial
<220> FEATURE:
<223> OTHER INFORMATION: binding site_pro at position 6,9,15 is
      Hydroxyproline

<400> SEQUENCE: 16

Gly Ala Ala Gly Pro Pro Gly Pro Pro Gly Ser Ala Gly Thr Pro Gly
1               5                   10                  15

Leu Gln


<210> SEQ ID NO 17
<211> LENGTH: 9
<212> TYPE: PRT
<213> ORGANISM: Artificial
<220> FEATURE:
<223> OTHER INFORMATION: collagen motif_pro at position 4 is
      Hydroxyproline

<400> SEQUENCE: 17

Arg Gly Gln Pro Gly Val Met Gly Phe
1               5
```

COLLAGEN-DERIVED RECOMBINANT PROTEINS WITH VON WILLEBRAND FACTOR-BINDING ACTIVITY

RELATED APPLICATION DATA

This application is a National Stage Application under 35 U.S.C. 371 of co-pending PCT application number PCT/EP2013/071816 designating the United States and filed Oct. 18, 2013; which claims the benefit of FR application number 1259996 and filed Oct. 19, 2012 each of which are hereby incorporated by reference in their entireties.

The invention relates to recombinant proteins comprising at least two collagen-derived motifs allowing these proteins to specifically bind von Willebrand factor (vWF). These proteins may be used in various in vitro biological tests in order to measure the ability of von Willebrand factor to bind collagen.

Von Willebrand factor is an adhesive glycoprotein made up of high molecular weight multimers produced by endothelial cells and megakaryocytes. It is stored in platelets and is present in circulating form in plasma. The mature von Willebrand protein consists of up to a hundred 250 kDa monomers assembled via disulfide bridges into multimers whose mass may reach about 20 MDa. Multimerization is a major process because if all multimers are able to bind factor VIII, whatever their size, high molecular weight multimers are the forms most active in ensuring platelet adhesion. Formation of these multimers is related to the presence in the monomer's sequence of so-called "structural" domains, namely a cysteine-rich domain (cysteine knot domain) and a D3 domain allowing optimal multimerization of von Willebrand factor dimers (Springer T A, *J Thromb Haemost.* 2011 July; 9 Suppl 1:130-43). There are several D domains in the monomer's sequence characterized by the presence of consensus sequences allowing disulfide isomerases to bind. Next to these "structural" domains are so-called "functional" domains including three domains—A1, A2 and A3—with the A1 and A3 domains containing a collagen-binding site, the A1 domain a platelet GpIb and αIIβIII receptor-binding site, and the A2 domain proteolytic cleavage sites (Schneppenheim R, *Thromb Res.* 2011; 128 Suppl 1:53-7).

The formation of von Willebrand multimers is controlled by the protein ADAMTS13 (a disintegrin and metalloprotease with thrombospondin motifs) by proteolytic cleavage at the A2 domain. A deficiency in ADAMTS13 leads to thrombotic thrombocytopenic purpura (TTP) resulting from platelet adhesion to very large von Willebrand factor multimers, causing platelet thrombi in microcirculation and hemolysis.

Von Willebrand factor plays two major roles by allowing 1) platelet adhesion following an endothelial lesion and the laying bare of collagen, this adhesion becoming highly von Willebrand factor-dependent in the presence of high flow rates or shearing forces, and 2) transport and protection of coagulation factor VIII in circulating blood. In plasma, its concentration is about 10 μg/ml and the plasma values of this factor are between 50 and 150 IU/di in activity.

Von Willebrand disease is the most common hemorrhagic disease, with a prevalence of about 1% in the general population. It is characterized by bleeding primarily in the mucous membranes. There are various types and sub-types of von Willebrand disease characterized by quantitative and qualitative deficiencies of this factor. Thus the following may be distinguished:

type 1, corresponding to a partial quantitative deficiency of von Willebrand factor. It represents 70 to 80% of affected patients, type 3, which corresponds to a total quantitative deficiency of this factor, associated with severe hemorrhages and a marked drop in factor VIII, type 2, corresponding to a qualitative deficiency of von Willebrand factor. It is divided into several subtypes, namely 1) subtype 2A, which has decreased affinity for platelets bound in the absence of high molecular weight multimers, 2) subtype 2B, characterized by increased affinity for platelet GpIb receptor, which results in elimination or loss of high molecular weight multimers, 3) subtype 2N, which has decreased affinity for factor VIII, resulting in a deficiency of factor VIII with a normal level of von Willebrand factor, and 4) subtype 2M, which encompasses all other types of functional deficiencies of von Willebrand factor not related to loss of high molecular weight multimers.

Von Willebrand factor plays a major role in the indirect interaction between platelet GpIb receptor and collagen. The high molecular weight multimeric forms allow recruitment of platelets at lesioned sites of vascular territories subjected to high flow rates. Von Willebrand factor binds collagen via its A3 and A1 domains, while the A1 domain also binds platelet GpIb receptor.

Collagens are the principal structural components of the extracellular matrix of all multicellular organisms. They are a protein family comprised of 28 different types playing a role during development and in tissue homeostasis. They are able to be assembled into various supramolecular structures in the form of fibrils, microfibrils or networks. Collagens have the common characteristic of containing one or more domains having a triple-helix structure made up of three polypeptide chains, or a chains, coiled around each other. This feature is made possible by the presence, in all three amino acids, of glycine in helical motifs consisting of repeated G-X-Y type sequences where X is often proline and Y hydroxyproline (Chen C and Raghunath M. *Fibrogenesis Tissue Repair.* 2009 Dec. 15; 2:7).

Type II and III collagens have a single, high affinity site for the von Willebrand factor A3 domain (Herr A B and Farndale R W, *J Biol Chem.* 2009 Jul. 24; 284(30):19781-5). This peptide motif is located between amino acids 403 and 413 and is composed of GPRGQOGVMGFO (SEQ ID NO:10) with certain critical amino acids for binding von Willebrand factor (Lisman T et al., *Blood.* 2006 Dec. 1; 108(12):3753-6). This peptide sequence is also involved in interactions between type II, III, IV collagen and receptors DDR1 and DDR2 (discoidin domain receptor) (Xu H et al., *Matrix Biol.* 2011 January; 30(1):16-26), expressed by epithelial cells and cells of mesenchymal origin, respectively, and with the protein SPARC (secreted protein acidic and rich in cysteine, also called osteonectin), involved in cell-extracellular matrix interactions (Giudici C et al., *J Biol Chem.* 2008 Jul. 11; 283(28):19551-60). More recently, Brondijk et al. described recognition motifs potentially involved in the binding of type I collagen to von Willebrand factor, namely the motif RGQAGVMF (SEQ ID NO:11) for the alpha-1 chain and RGEOGNIGF (SEQ ID NO:12) for the alpha-2 chain, which are so-called "degenerate" motifs with respect to the motif RGQOGVMGF (SEQ ID NO:17) present in the type III collagen sequence (Brondijk T H et al. *Proc Natl Acad Sci USA.* 2012 Apr. 3; 109(14):5253-8). Furthermore, Verkleij et al. have identified as a potential binding site amino acids 541 to 558 consisting of GAAGPOGPOGSAG-TOGLQ (SEQ ID NO:16) (Verkleij et al., *Blood.* 1998 May 15; 91(10):3808-16). This peptide motif is located between the von Willebrand motif described by Lisman et al. and the α1β2 integrin binding motif (GMOGER) (SEQ ID NO:13). This motif was not taken up again in other subsequent work.

It should be noted that Bonnefoy et al. showed that the von Willebrand factor A1 domain could replace the A3 domain in order to allow platelets to bind collagen at high flow rates, although they have not specified since whether this interaction was carried out at the same collagen binding site as for the A3 domain (Bonnefoy A et al. *J Thromb Haemost.* 2006 October; 4(10):2151-61).

Classifying patients suffering from von Willebrand disease requires the use of various laboratory tests. Assaying von Willebrand factor antigen (vWF:Ag) is often carried out as a first course when suspicion arises but it does not make it possible to quantify von Willebrand factor activity. Recourse to so-called functional tests that measure von Willebrand factor activity is essential for detecting functional deficiencies of von Willebrand factor and for classifying patients in the various subtypes, in particular when these anomalies are not associated with a low concentration of von Willebrand factor. As specified above, von Willebrand factor allows platelets to adhere to collagen by establishing a bond between collagen and platelet GpIb receptor. The functional tests used to date target in particular the von Willebrand factor/platelet bond.

Measuring von Willebrand factor collagen-binding is not routinely used, primarily because current tests are not suited to the urgency and case-by-case nature of the problem. However, measuring von Willebrand factor collagen-binding, or vWF:CB (von Willebrand factor:collagen binding) is more sensitive for detecting the presence of high molecular weight von Willebrand factor (Favaloro E J, *Thromb Haemost.* 2010 November; 104(5):1009-21).

In order to facilitate the classification of patients by subtype, one calculates the relationship (ratio) between the binding activity of von Willebrand factor to platelets or collagen to von Willebrand factor and the concentration of von Willebrand factor antigen (vWF:Ag). An activity/Ag ratio equal or superior to 0.7 is obtained for normal and type I patients and a ratio inferior to 0.7 is characteristic of subtypes 2A, 2B and 2M. Subtype 2N cannot be detected by this measurement.

ELISA tests based on measuring von Willebrand factor collagen-binding permit good discrimination between type 1 and type 2A/2B patients (Favaloro E J, *Thromb Haemost.* 2010 November; 104(5):1009-21) and between types 2A and 2M (Baronciani L et coll. *J Thromb Haemost.* 2006 September; 4(9):2088-90).

Although these results appear encouraging, a debate exists regarding the advantage of this test for classifying patients. This debate relates mainly to characterization of the absence or presence of high molecular weight multimers, which is an important issue in terms of helping to classify both von Willebrand disease patients and those patients having an acquired deficiency of high molecular weight multimers. There are to date no less than 7 ELISA kits on the market, not counting those developed in-house by certain laboratories. These kits use collagen preparations of different origins and natures, which complicates the comparison of results between the various studies. To this is added the lack of homogeneity between the batches produced. The collagens typically used are type I, type III, type IV and type VI collagen. These collagens of animal origin are not 100% pure and may be the cause of the conflicting results described. The result is a significant need for standardization of the collagen preparations used, both for ELISA tests and for tests measuring von Willebrand factor collagen-binding in flow conditions. This point was amply detailed and discussed in a directive of the ISTH biorheology subcommittee moving toward standardization of tests using collagen (Heemskerk J W M et al. *J Thromb Haemost.* 2011 April; 9(4):856-8).

The engineering of extracellular matrix-derived proteins makes it possible today to have proteins with properties equal to native proteins (Werkmeister J and Ramshaw *J. Biomed Mater.* 2012 February; 7(1):012002). Using recombinant DNA technologies, it is possible to obtain, in a reproducible manner, stable batches of these proteins in very large amounts. Although native collagens have already been produced successfully in eukaryotic cells (patent EP 2383338), the production of collagen-derived recombinant proteins arising from an engineering process is a recent approach that has not been used to date to produce collagen-derived proteins able to bind von Willebrand factor and to be used in a test of activity of this factor, such as the polypeptides of the present invention.

Unlike the test of von Willebrand factor platelet GpIb receptor-binding activity that exists in automated form, there is to date no automated test for measuring von Willebrand factor collagen-binding. Automated tests are generally based on the principle of aggregation of particles coated with a reagent. The aggregation test used most in diagnostics uses latex beads that, as yet, cannot be coated with collagen for use as reagent. The physicochemical properties of the collagens typically used and, in particular, the fact of being soluble only at acidic pH, complicate the use of this type of beads. Conversely, the polypeptides according to the invention are soluble at physiological pH, allowing optimal adsorption on the particle surface. Furthermore, their mass is smaller than that of native collagens, which should allow better adsorption on the particles. Finally, the potential addition via engineering of cysteines in the polypeptide sequence makes it possible to carry out targeted grafting between a particle functionalized with a maleimide type functional group on the particle surface and the cysteine present in the protein. The specific advantages of the polypeptides according to the invention coupled with their activity allow the development of the first automated test for measuring plasma von Willebrand factor collagen-binding.

SUMMARY OF THE INVENTION

The present invention has as an object a method for determining von Willebrand factor collagen-binding activity in a biological sample comprising the following steps:

a) Providing a polypeptide selected from:
  - the polypeptide comprising the sequence from position 24 to position 184 of SEQ ID NO: 2,
  - the polypeptide comprising the sequence from position 24 to position 205 of SEQ ID NO: 4,
  - the polypeptide comprising the sequence from position 24 to position 226 of SEQ ID NO: 5,
  - a von Willebrand factor-binding polypeptide comprising the peptide motif $Z_1$-GPRGQPGVMGFP (SEQ ID NO:6)-$Z_2$-GPRGQPGVMGFP (SEQ ID NO:6) and the peptide motif $(GPP)_k$ (SEQ ID NO:15)
  - wherein independently
  - $Z_1$ represents a linker comprising 6 to 12 amino acids,
  - $Z_2$ represents a linker comprising 6 to 12 amino acids,
  - k is an integer between 4 and 15;

b) Contacting the biological sample with the aforesaid polypeptide;

c) Measuring the binding of von Willebrand factor in the biological sample to the polypeptide of step a) in order to measure von Willebrand factor collagen-binding activity.

The polypeptides described above have von Willebrand factor-binding activity and affinity equal to that of type I and III collagens. These polypeptides have advantageous physicochemical features, in particular the fact that they are stable at physiological pH, and also that they are able to bind von Willebrand factor in non-fibrillar form.

Preferably, $Z_1$ and $Z_2$ independently represent a peptide motif of formula $(GAA_1AA_2)_{n1}(GAA_3AA_4)_{n2}(GAA_5AA_6)_{n3}(GAA_7AA_8)_{n4}$ (SEQ ID NO:14)

wherein independently:

$AA_1$, $AA_3$, $AA_5$ and $AA_7$ independently represent amino acids D or A, $AA_2$, $AA_4$, $AA_6$ and $AA_8$ independently represent amino acids A or P, $n_1$, $n_2$, $n_3$ and $n_4$ are independently selected from 0, 1, 2, 3 or 4 and the sum $n_1+n_2+n_3+n_4$ is equal to 2, 3 or 4.

More preferentially, $Z_1$ and $Z_2$ represent the peptide motif GDAGAPGAP of SEQ ID NO: 7.

A second object of the present invention is a method for diagnosing von Willebrand disease in a patient, comprising the following steps:

a) Providing a polypeptide selected from:

the polypeptide comprising the sequence from position 24 to position 184 of SEQ ID NO: 2, the polypeptide comprising the sequence from position 24 to position 205 of SEQ ID NO: 4, the polypeptide comprising the sequence from position 24 to position 226 of SEQ ID NO: 5, a von Willebrand factor-binding polypeptide comprising the peptide motif $Z_1$-GPRGQPGVMGFP(SEQ ID NO:6)-$Z_2$-GPRGQPGVMGFP(SEQ ID NO:6) and the peptide motif $(GPP)_k$ (SEQ ID NO:15)

wherein independently $Z_1$ represents a linker comprising 6 to 12 amino acids, $Z_2$ represents a linker comprising 6 to 12 amino acids, k is an integer between 4 and 15;

b) Contacting a biological sample previously taken from the patient with the aforesaid polypeptide;

c) Measuring the binding of von Willebrand factor present in the biological sample to the polypeptide of step a) in order to measure von Willebrand factor collagen-binding activity.

Advantageously, the diagnostic method is used to diagnose von Willebrand disease types 1, 2, 2A, 2B, 2M and 3.

Preferentially, $Z_1$ and $Z_2$ independently represent a peptide motif of formula $(GAA_1AA_2)_{n1}$ $(GAA_3AA_4)_{n2}$ $(GAA_5AA_6)_{n3}(GAA_7AA_8)_{n4}$ (SEQ ID NO:14)

wherein independently $AA_1$, $AA_3$, $AA_5$ and $AA_7$ independently represent amino acids D or A, $AA_2$, $AA_4$, $AA_6$ and $AA_8$ independently represent amino acids A or P, $n_1$, $n_2$, $n_3$ and $n_4$ are independently selected from 0, 1, 2, 3 or 4 and the sum $n_1+n_2+n_3+n_4$ is equal to 2, 3 or 4.

More preferentially, $Z_1$ and $Z_2$ represent the peptide motif GDAGAPGAP of SEQ ID NO: 7.

In advantageous embodiments of the invention, the methods for diagnosing von Willebrand disease further comprise determining the quantity of von Willebrand factor present in the biological sample.

Preferably, the polypeptide of step a) is attached to a solid support.

Preferably, steps b) and c) are carried out in flow conditions.

The invention also has as an object a polypeptide selected from:

the polypeptide comprising the sequence of SEQ ID NO: 2, the polypeptide comprising the sequence from position 24 to position 184 of SEQ ID NO: 2, the polypeptide comprising the sequence of SEQ ID NO: 4, the polypeptide comprising the sequence from position 24 to position 205 of SEQ ID NO: 4, the polypeptide comprising the sequence of SEQ ID NO: 5, the polypeptide comprising the sequence from position 24 to position 226 of SEQ ID NO: 5, a von Willebrand factor-binding polypeptide comprising the peptide motif $Z_1$-GPRGQPGVMGFP(SEQ ID NO:6)-$Z_2$-GPRGQPGVMGFP(SEQ ID NO:6) and the peptide motif $(GPP)_k$ (SEQ ID NO:15)

wherein independently $Z_1$ represents a linker comprising 6 to 12 amino acids, $Z_2$ represents a linker comprising 6 to 12 amino acids, k is an integer between 4 and 15.

In preferred embodiments, the polypeptides according to the present invention are attached to a solid support.

The invention also has as an object kits for determining von Willebrand factor collagen-binding activity, comprising a polypeptide selected from:

the polypeptide comprising the sequence from position 24 to position 184 of SEQ ID NO: 2, the polypeptide comprising the sequence from position 24 to position 205 of SEQ ID NO: 4, the polypeptide comprising the sequence from position 24 to position 226 of SEQ ID NO: 5, a von Willebrand factor-binding polypeptide of at least 100 amino acids comprising the peptide motif $Z_1$-GPRGQPGVMGFP(SEQ ID NO:6)-$Z_2$-GPRGQPGVMGFP(SEQ ID NO:6) and the peptide motif $(GPP)_k$ (SEQ ID NO:15)

wherein independently $Z_1$ represents a linker comprising 6 to 12 amino acids, $Z_2$ represents a linker comprising 6 to 12 amino acids, k is an integer between 4 and 15;

a detection reagent for determining von Willebrand factor collagen-binding.

Advantageously, the kits according to the present invention further comprise a von Willebrand factor-binding antibody.

Preferably, the polypeptide is attached to a solid support.

SEQUENCE LISTING

SEQ ID NO: 1—Polynucleotide encoding a polypeptide comprising two von Willebrand factor-binding motifs SEQ ID NO: 2—Polypeptide comprising two von Willebrand factor-binding motifs SEQ ID NO: 3—Polypeptide comprising one von Willebrand factor-binding motif SEQ ID NO: 4—Polypeptide comprising three von Willebrand factor-binding motifs SEQ ID NO: 5—Polypeptide comprising four von Willebrand factor-binding motifs SEQ ID NO: 6—Von Willebrand factor-binding motif SEQ ID NO: 7—Linker SEQ ID NO: 8—Linker-Von Willebrand factor-binding motif-Linker-Von Willebrand factor-binding motif

DETAILED DESCRIPTION OF THE INVENTION

Von Willebrand factor binds collagen and changes in this factor's collagen-binding activity are the cause of the various types of von Willebrand disease. Collagen is a protein that is difficult to produce or purify and that is not easy to handle. Indeed, due to its structure, collagen adheres to surfaces and it is not water-soluble. The present invention proposes recombinant polypeptides able to replace collagen in all tests and kits for measuring von Willebrand factor collagen-binding. The polypeptides of the present invention may be produced in various cell systems, including CHO cells. They are easily purified and in solution form trimers whose structure is similar to that of collagen. These polypeptides are in addition soluble, in particular at physiological pH, which makes it possible to easily attach them to solid supports such as, for example, latex beads.

Remarkably, the experimental data reported below shows that the polypeptides according to the invention have von Willebrand factor-binding activity and affinity equal to that of human type III collagen. The polypeptides according to the present invention thus have numerous applications in methods, tests and kits based on determining/measuring von Willebrand factor collagen-binding.

The invention first relates to von Willebrand factor-binding polypeptides selected from:

- the polypeptide of SEQ ID NO: 2,
- the polypeptide from position 24 to position 184 of SEQ ID NO: 2,
- the polypeptide of SEQ ID NO: 4,
- the polypeptide from position 24 to position 205 of SEQ ID NO: 4,
- the polypeptide of SEQ ID NO: 5,
- the polypeptide from position 24 to position 226 of SEQ ID NO: 5,
- a von Willebrand factor-binding polypeptide comprising the peptide motif $Z_1$-(SEQ ID NO:6)-$Z_2$-(SEQ ID NO:6) and the peptide motif $(GPP)_k$ (SEQ ID NO:15) wherein independently $Z_1$ represents a linker comprising 6 to 12 amino acids, $Z_2$ represents a linker comprising 6 to 12 amino acids, k is an integer between 4 and 15.

The invention also relates to von Willebrand factor-binding polypeptides selected from:

- the polypeptide comprising the sequence of SEQ ID NO: 2,
- the polypeptide comprising the sequence from position 24 to position 184 of SEQ ID NO: 2,
- the polypeptide comprising the sequence of SEQ ID NO: 4,
- the polypeptide comprising the sequence from position 24 to position 205 of SEQ ID NO: 4,
- the polypeptide comprising the sequence of SEQ ID NO: 5,
- the polypeptide comprising the sequence from position 24 to position 226 of SEQ ID NO: 5,
- a von Willebrand factor-binding polypeptide comprising the peptide motif $Z_1$-GPRGQPGVMGFP(SEQ ID NO:6)-$Z_2$-GPRGQPGVMGFP(SEQ ID NO:6) and the peptide motif $(GPP)_k$ (SEQ ID NO:15)

wherein independently $Z_1$ represents a linker comprising 6 to 12 amino acids, $Z_2$ represents a linker comprising 6 to 12 amino acids, k is an integer between 4 and 15.

Preferably, $Z_1$ and $Z_2$ independently represent a peptide motif of formula $(GAA_1AA_2)_{n1}(GAA_3AA_4)_{n2}(GAA_5AA_6)_{n3}(GAA_7AA_8)_{n4}$ (SEQ ID NO:14)

wherein independently $AA_1$, $AA_3$, $AA_5$ and $AA_7$ independently represent amino acids D or A, $AA_2$, $AA_4$, $AA_6$ and $AA_8$ independently represent amino acids A or P, $n_1$, $n_2$, $n_3$ and $n_4$ are independently selected from 0, 1, 2, 3 or 4 and the sum $n_1+n_2+n_3+n_4$ is equal to 2, 3 or 4. More preferentially, $Z_1$ and $Z_2$ represent the peptide motif GDAGAPGAP of SEQ ID NO: 7.

The polypeptides according to the present invention comprise at least two von Willebrand factor-binding motifs of formula GPRGQPGVMGFP (SEQ ID NO: 6) separated by a linker. Such linkers are described below.

Preferably, the polypeptides according to the present invention comprise a motif of type GPRGQPGVMGFP (SEQ ID NO: 6)-Linker-GPRGQPGVMGFP(SEQ ID NO: 6) and more preferentially a motif of type "Linker-GPRGQPGVMGFP(SEQ ID NO: 6)-Linker-GPRGQPGVMGFP(SEQ ID NO: 6)-Linker".

In a preferred embodiment of the invention, the polypeptides comprise a motif of type $(GPP)_k$-Linker-GPRGQPGVMGFP(SEQ ID NO: 6)-Linker-GPRGQPGVMGFP(SEQ ID NO: 6) or a motif of type GPRGQPGVMGFP(SEQ ID NO: 6)-Linker-GPRGQPGVMGFP(SEQ ID NO: 6)-Linker-$(GPP)_k$ (SEQ ID NO:15).

In an embodiment of the present invention, the polypeptides according to the present invention comprise the motif of SEQ ID NO: 8.

Any amino acid sequence may be used as a linker. Preferably, the linker comprises 6-12 amino acids.

In a preferred embodiment, the linker represents a peptide motif of formula $(GAA_1AA_2)_{n1}$ $(GAA_3AA_4)_{n2}(GAA_5AA_6)_{n3}(GAA_7AA_8)_{n4}$ (SEQ ID NO:14)

wherein independently $AA_1$, $AA_3$, $AA_5$ and $AA_7$ independently represent amino acids D or A, $AA_2$, $AA_4$, $AA_6$ and $AA_8$ independently represent amino acids A or P, $n_1$, $n_2$, $n_3$ and $n_4$ are independently selected from 0, 1, 2, 3 or 4 and the sum $n_1+n_2+n_3+n_4$ is equal to 2, 3 or 4. More preferentially, the linker represents peptide motif GDAGAPGAP of SEQ ID NO: 7.

The peptide motif of formula $(GPP)_k$ (SEQ ID NO:15), wherein k is an integer between 4 and 15, allows the trimerization of the polypeptide according to the present invention. Preferably, in the formula $(GPP)_k$ (SEQ ID NO:15), k is equal to 10. This detrimerization motif is advantageously located at one of the ends of the polypeptide in relation to the von Willebrand factor-binding motif and is separated from the latter by a variable number of amino acids.

The invention also relates to polypeptides having at least 50%, 60%, 70%, 80%, 85%, 90%, 95% identity with one of the following polypeptides:

- the polypeptide of SEQ ID NO: 2,
- the polypeptide from position 24 to position 184 of SEQ ID NO: 2,
- the polypeptide of SEQ ID NO: 4,
- the polypeptide from position 24 to position 205 of SEQ ID NO: 4,
- the polypeptide of SEQ ID NO: 5, the polypeptide from position 24 to position 226 of SEQ ID NO: 5.

By identical amino acids is meant invariant or unchanged amino acids between two sequences. These polypeptides may have a deletion, an addition or a substitution of at least one amino acid in comparison with the reference polypeptide.

By "percent identity" between two amino acid sequences is meant, in the meaning of the present invention, a percentage of identical amino acid residues between the two sequences to be compared, obtained after the best alignment (optimal alignment), this percentage being purely statistical and the differences between the two sequences being distributed randomly over their entire length. This percent identity between two polypeptides may be determined by a global identity algorithm such as described by Needleman and Wunsch (1970).

Preferably, polypeptides having a percent identity with the polypeptides of the present invention retain the properties of the reference polypeptide. Preferably, these polypeptides retain their ability to bind von Willebrand factor and their water solubility, in particular at physiological pH.

The polypeptides of the present invention typically comprise between 150 and 300 amino acids.

For use in von Willebrand factor-binding tests, the polypeptides of the present invention may be attached to any type of solid support such as microplates for ELISA tests or beads, including latex beads or gold beads.

The invention also has as an object polynucleotides encoding the polypeptides of the present invention such as the polynucleotide of SEQ ID NO: 1.

The present invention also has as an object a method for determining von Willebrand factor collagen-binding activity in a biological sample comprising the following steps:

a) Providing a polypeptide selected from:
  - the polypeptide comprising the sequence from position 24 to position 184 of SEQ ID NO: 2,
  - the polypeptide comprising the sequence from position 24 to position 205 of SEQ ID NO: 4,
  - the polypeptide comprising the sequence from position 24 to position 226 of SEQ ID NO: 5,
  - a von Willebrand factor-binding polypeptide comprising the peptide motif $Z_1$-GPRGQPGVMGFP(SEQ ID NO: 6)-$Z_2$-GPRGQPGVMGFP(SEQ ID NO: 6) and the peptide motif $(GPP)_k$ (SEQ ID NO:15)

wherein independently $Z_1$ represents a linker comprising 6 to 12 amino acids, $Z_2$ represents a linker comprising 6 to 12 amino acids, k is an integer between 4 and 10;

b) Contacting the biological sample with the aforesaid polypeptide;

c) Measuring the binding of von Willebrand factor in the biological sample to the polypeptide of step a).

In the last step of the method, measurement of the binding of von Willebrand factor in the biological sample to the polypeptide according to the invention gives a measurement of von Willebrand factor collagen-binding and in particular human type III collagen-binding.

This method may be used with the polypeptides according to the present invention as described above.

The invention also relates to a diagnostic method in a patient suffering from or suspected of suffering from a type of von Willebrand disease, comprising the following steps:

a) Providing a polypeptide selected from:
  - the polypeptide comprising the sequence from position 24 to position 184 of SEQ ID NO: 2,
  - the polypeptide comprising the sequence from position 24 to position 205 of SEQ ID NO: 4,
  - the polypeptide comprising the sequence from position 24 to position 226 of SEQ ID NO: 5,
  - a von Willebrand factor-binding polypeptide comprising the peptide motif $Z_1$-GPRGQPGVMGFP(SEQ ID NO: 6)-$Z_2$-GPRGQPGVMGFP(SEQ ID NO: 6) and the peptide motif $(GPP)_k$ (SEQ ID NO:15)

wherein independently $Z_1$ represents a linker comprising 6 to 12 amino acids, $Z_2$ represents a linker comprising 6 to 12 amino acids, k is an integer between 4 and 10;

b) Contacting a biological sample previously taken from the patient with the aforesaid polypeptide;

c) Measuring the binding of von Willebrand factor present in the biological sample to the polypeptide of step a).

The invention also relates to a diagnostic method in a patient suffering from or suspected of suffering from a type of von Willebrand disease, comprising the following steps:

a) Taking a biological sample from the patient, b) Contacting the biological sample taken from the patient with a polypeptide selected from:
  - the polypeptide comprising the sequence from position 24 to position 184 of SEQ ID NO: 2,
  - the polypeptide comprising the sequence from position 24 to position 205 of SEQ ID NO: 4,
  - the polypeptide comprising the sequence from position 24 to position 226 of SEQ ID NO: 5,
  - a von Willebrand factor-binding polypeptide comprising the peptide motif $Z_1$-GPRGQPGVMGFP(SEQ ID NO: 6)-$Z_2$-GPRGQPGVMGFP(SEQ ID NO: 6) and the peptide motif $(GPP)_k$ (SEQ ID NO:15)

wherein independently $Z_1$ represents a linker comprising 6 to 12 amino acids, $Z_2$ represents a linker comprising 6 to 12 amino acids, k is an integer between 4 and 15;

c) Measuring the binding of von Willebrand factor present in the biological sample to the polypeptide of step a).

In the methods of the present invention, the last step of the method comprising measurement of the binding of von Willebrand factor in the biological sample to the polypeptide according to the invention gives a measurement of von Willebrand factor collagen-binding and in particular human type III collagen-binding.

These methods may be used with the polypeptides according to the present invention as described above.

By sample is meant in particular any sample containing or likely to contain von Willebrand factor whose collagen-binding activity, and in particular human type III collagen-binding activity, is sought to be determined. The sample may in particular be a biological sample taken beforehand from a patient. In preferred embodiments, the biological sample is blood, plasma, platelet-rich plasma, biological tissue, a biological organ or bodily fluid.

The methods according to the present invention comprise contacting the sample with at least one polypeptide according to the present invention. This contacting is carried out according to standard methods well known to a person skilled in the art. This contacting is thus typically carried out in aqueous medium and more preferentially in buffer that guarantees the three-dimensional stability of the polypeptides and that is protease-free. In a preferred embodiment, this step is carried out in phosphate buffer.

Advantageously, the polypeptide according to the invention may be attached to a solid support. The polypeptide may be attached to any type of natural or synthetic support, in particular any natural or synthetic polymer. This solid support is, for example, selected from plastic, polystyrene, glass, metal.

In an embodiment, the polypeptide according to the invention is attached in at least one well of an ELISA-type microplate, for example.

In another embodiment, the polypeptide is attached to glass, plastic, polymer or metal beads, such as gold or latex beads, in particular by adsorption or covalent bonding.

The binding of von Willebrand factor in the biological sample to the polypeptide according to the invention is measured according to any suitable method. These methods are well known to a person skilled in the art. In particular, mention may be made of ELISA methods or agglutination and aggregation tests and tests in flow conditions.

This measurement may be made under static conditions in the absence of any disturbance of the medium in which binding occurs.

In other embodiments, binding is measured in flow conditions in order to reproduce the conditions of circulating blood. This determination makes it possible to measure the von Willebrand factor binding-activity of human or animal collagens of different types (types I, II, III, VI, for example) under the physiological conditions of circulating blood. Equipment and methods for taking these measurements, such as surface plasmon resonance, are well known to a person skilled in the art.

The measurement of von Willebrand factor-binding of the polypeptides according to the invention may be sufficient to establish a diagnosis of von Willebrand disease. In particular, the methods according to the present invention make it possible to establish the diagnosis of von Willebrand disease types 1, 2, 2A, 2B, 2M and 3.

In certain embodiments, the methods according to the invention further comprise quantification of von Willebrand factor present in the sample. This quantification may be carried out according to any customary technique. In an embodiment, this quantification of von Willebrand factor in the biological sample is carried out using antibodies directed against von Willebrand factor. In this embodiment, the method according to the invention comprises measurement of von Willebrand factor activity and more particularly its collagen-binding activity (functional assay) and measurement of the quantity of von Willebrand factor present in the biological sample (quantitative assay).

Typically, measurement of von Willebrand factor collagen-binding activity combined with quantification of von Willebrand factor in the sample makes it possible to determine the ratio:

$$R = \frac{\text{von Willebrand factor bound to the polypeptide (activity)}}{\text{von Willebrand factor present in the biological sample (antigen)}}.$$

The determination of this ratio makes it possible in particular to establish a diagnosis or to refine a diagnosis of von Willebrand disease and, more particularly, to distinguish von Willebrand disease types 1 and 3 (quantitative deficiency) and type 2 (qualitative deficiency). The methods of the present invention also make it possible to distinguish and/or establish a diagnosis of von Willebrand disease types 1, 2, 2A, 2B, 2M and 3.

The invention also relates to kits for determining von Willebrand factor collagen-binding activity comprising a polypeptide as described above. Preferentially, the polypeptide is attached to a solid support such as a latex bead or a gold bead.

The kit further comprises a detection reagent for determining von Willebrand factor collagen-binding. This detection reagent may be any reagent typically used. It may be a label such as a fluorophore attached to the polypeptide according to the present invention. In an embodiment, it is an antibody attached to the polypeptide according to the invention or to von Willebrand factor. This antibody may be labeled in order to facilitate its detection. Preferably, the kit further comprises a von Willebrand factor-binding antibody.

FIGURES

FIG. 1: Protein profile representing purified fractions of the polypeptide according to the invention (SEQ 2) pepsin-digested or not. N=undigested normal fraction, P=pepsin-digested fraction and M=molecular weight marker. In fraction N, we observe a majority band of 70 kDa, which is found in fraction P. This band thus corresponds to the polypeptide according to the invention with a triple-helix structure.

Figure 2:
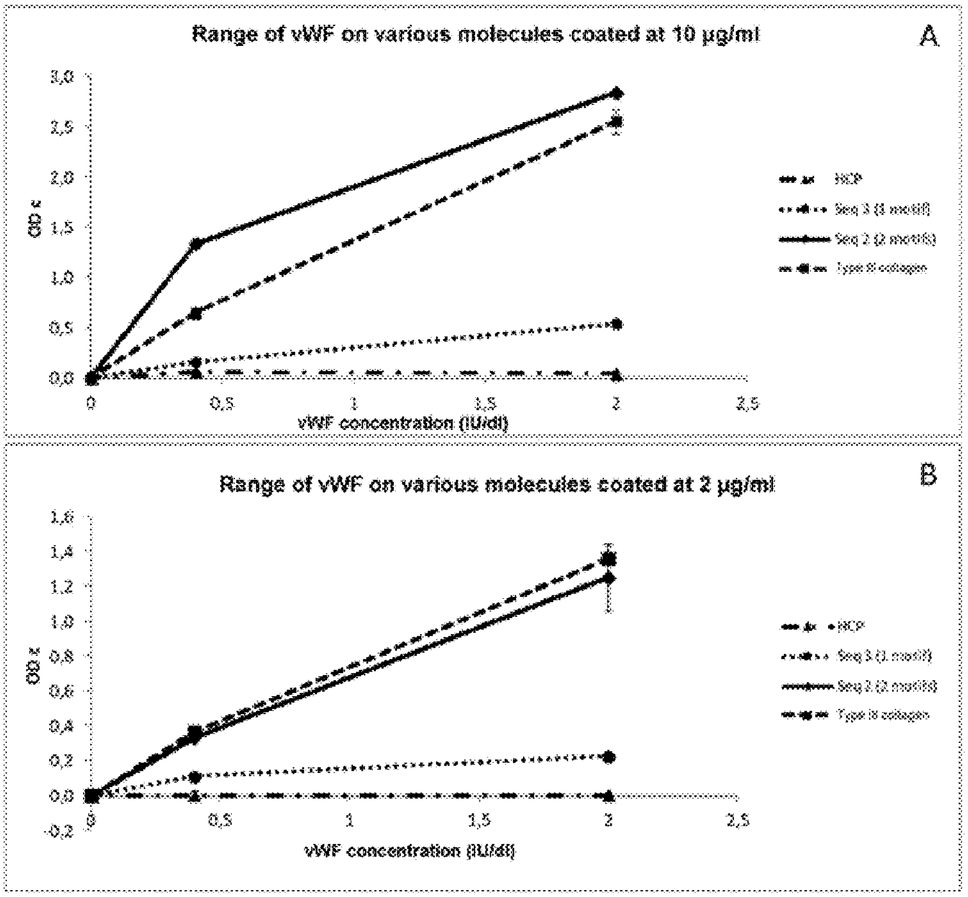

FIG. 2: Measurement of purified von Willebrand factor (Wilfactin)-binding activity on various polypeptides according to the invention having one (SEQ 3) motif or two (SEQ 2) motifs and on type III collagen used as a reference (BD Biosciences) and on endogenous proteins or HCP (host cell protein) used as a negative control. A=polypeptides coated at 10 μg/ml and B=polypeptides coated at 2 μg/ml. It is observed that at least 2 von Willebrand factor-binding motifs are needed to obtain von Willebrand factor-binding equal to that of native type III collagen. Mean±SD with n=2.

Figure 3:
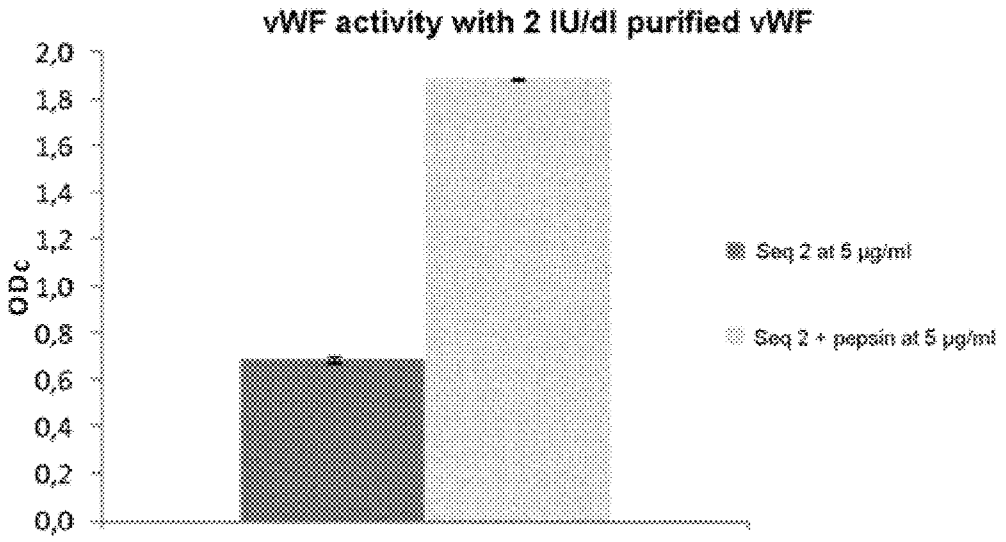

FIG. 3: Measurement of von Willebrand factor (Wilfactin)-binding at 2 IU/dl on the polypeptide according to the invention (SEQ 2) pepsin-digested or not and coated at 2 μg/ml. A 3-fold increase in von Willebrand factor-binding activity is observed when the polypeptide according to the invention is pepsin-digested. Mean±SD with n=2.

Figure 4:
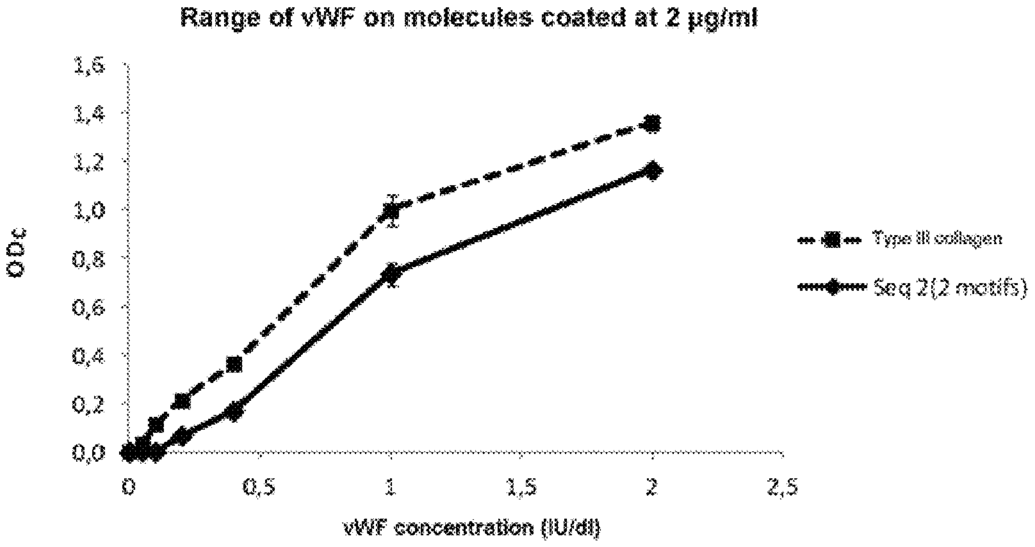

FIG. 4: Measurement of binding to the polypeptide according to the invention (SEQ 2) and to type III collagen coated at 2 μg/ml for various concentrations of von Willebrand factor (0, 0.05, 0.1, 0.2, 0.4, 1 and 2 IU/dl). The polypeptide according to the invention has the same von Willebrand factor-binding activity and the same sensitivity as native type III collagen. Mean±SD with n=2.

Figure 5:
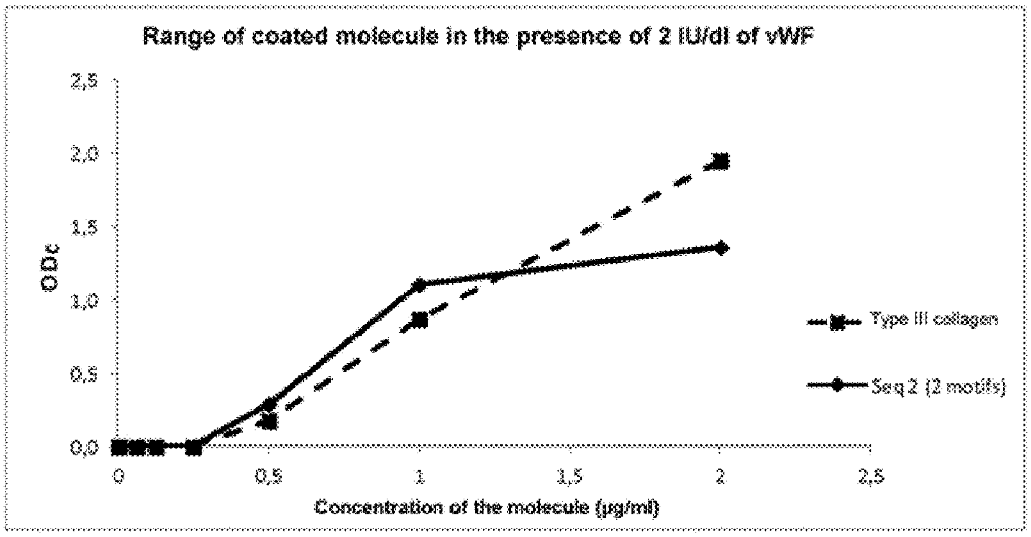

FIG. 5: Measurement of the binding of von Willebrand factor used at 2 IU/dl to various concentrations of the polypeptide according to the invention (SEQ 2) and to type III collagen (0, 0.032, 0.062, 0.125, 0.25, 0.5, 1 and 2 μg/ml). Mean±SD with n=2.

Figure 6:
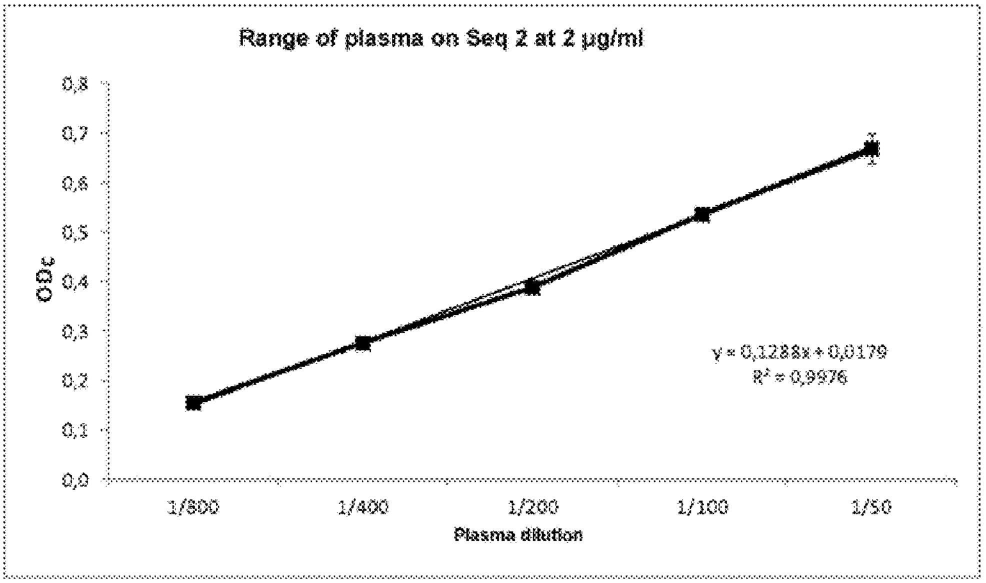

FIG. 6: Measurement of the binding of plasma von Willebrand factor to the polypeptide according to the invention coated at 2 μg/ml for various dilutions of control plasma. The results show a linearity of binding of von Willebrand factor to the polypeptide according to the invention with a linear regression curve having an $R^2$ of 0.9976. Good reproducibility of the results obtained with the polypeptide according to the invention is also observed. Mean±SD with n=10.

EXAMPLES

Example 1

Construction of the Vector Encoding the Polypeptide According to the Invention Containing a 6×His Tag The nucleotide sequence encoding the polypeptides according to the invention comes from the vector pUC57-

NVH020B containing type III collagen signal peptide (position 1 to 23 of the nucleotide sequence of the polypeptide according to the invention). This sequence is inserted in an expression vector dedicated to mammalian cells: pcDNA3.1+(Invitrogen). This vector contains, inter alia, the following elements:

- A CMV promoter,
- A multiple cloning site for inserting the nucleotide sequence of interest,
- A geneticin resistance cassette for expression in mammalian cells,
- An ampicillin resistance cassette for expression in bacteria.

To allow insertion of the polypeptide according to the invention, restriction sites were inserted on each side of the nucleotide sequence. These are the 5' NheI restriction site and the 3' BamHI restriction site. To facilitate purification of the polypeptide according to the invention, a 6× histidine tag is added at the 5' or 3' end of the polypeptide sequence. In order to be able to subsequently remove this tag, a TEV (tobacco etch virus) cleavage sequence was inserted between the nucleotide sequence of the 6× histidine tag and the sequence encoding the polypeptide according to the invention.

All the final plasmids are sequenced to verify that no mutation was introduced in the DNA of the protein of interest and in the elements provided.

Example 2

Expression in CHO Cells of the Fusion Protein According to the Invention

CHO-S cells (Invitrogen) are pre-cultured for 3 weeks prior to transfection. The cells are maintained in dedicated CHO cell medium (Power-CHO, EXCEL 302, proCHO4, proCHO5, etc.) supplemented with 4 mM L-glutamine (Lonza) and 1× proHT (Lonza) in a 125 ml shake flask and shaken (80 rpm) in an incubator at 37° C. with 5% $CO_2$. Two days before transfection, the cells increased to $5\times10^5$ viable cells/ml by a complete change of the medium used and grown in 12.5 ml of complete dedicated CHO cell medium in a 125 ml shake flask.

The day of transfection, $5\times10^6$ viable cells are pelleted by centrifugation (5 min at 1000 g), then taken up in 5 ml of RPMI medium (Lonza) supplemented with 4 mM L-glutamine (Lonza) and 1× ProHT (Lonza). Four ml of suspension is then distributed in four 25 ml shake flasks (1 ml per flask) containing 9 ml of complete RPMI medium ($1\times10^6$ viable cells per shake flask). The CHO-S cells are then transfected with the vector containing the sequence encoding the polypeptide according to the invention described above. A positive transfection control is prepared by transfecting the cells with the vector pMAX-GFP and a negative transfection control is prepared by transfecting the cells with a vector lacking the geneticin resistance cassette. Transfection is carried out using the transfection agent Fecturin (PolyPlus Transfection) or any other suitable transfection agent according to the product's optimized commercial protocol. For Fecturin, the transfection conditions selected are 6 μg of DNA for 12 μl of Fecturin (ratio of DNA to transfection agent=½). A person skilled in the art will be able to define the transfection agent most suitable for so-called transient transfection or so-called stable transfection. Whether so-called transient or stable transfection is used, the cells are incubated in the presence of transfection complexes in static conditions at 37° C. and 5% $CO_2$. At 4 hours post-transfection the cells are resuspended in complete dedicated CHO cell medium, and at 24 hours post-transfection transfection efficiency is quantified on the positive and negative transfection controls using flow cytometry.

To produce the polypeptide according to the invention in so-called transient mode, a first sample of supernatant is taken at day 3 and then growth is stopped at day 5. The medium containing the polypeptide according to the invention secreted by the cells is collected after centrifugation at 3000 g for 10 minutes, allowing the cells to be removed, and then frozen at −20° C.

To produce the polypeptide according to the invention in a so-called stable culture, the cells are resuspended and then counted at 48 hours post-transfection. The totality of the cells is then centrifuged at 1000 g for 5 minutes and then inoculated at $3\times10^5$ viable cells/ml in dedicated CHO cell medium supplemented with 700 μg/ml geneticin (G418 Merck). The cells are then maintained three times per week. The totality of the cells is inoculated in 12.5 ml final of complete medium plus G418 in 125 ml shake flasks. A decrease in cell concentration and/or cell viability is observed in the first week of growth under selective pressure. Cell viability increases again after 2-3 weeks under selective pressure. When the culture reaches more than 95% viability, 10 ampoules containing $5\times10^6$ viable cells/ampoule are cryopreserved. The cells are frozen in dedicated CHO cell medium plus 20% DMSO.

Example 3

Production in CHO Cells of the Fusion Protein According to the Invention

Cells modified genetically to produce the polypeptide according to the invention are thawed and maintained in a suitable medium. The cells are maintained at $3\times10^5$ viable cells/ml for one or two weeks. The cells are placed in 12.5 ml of final medium in a 125 ml shake flask in a Kühner Lab-Therm® shaker with shaking at 80 rpm, set to 5% $CO_2$ and with humidity between 40 and 80%. Next, the cells are amplified in order to have the quantity necessary to carry out production. Amplification consists in maintaining the cells in greater volumes at each maintenance step in order to keep all the cells at a viable concentration.

When the quantity of cells needed for production is obtained, production may be started. The cells are inoculated at $3\times10^5$ viable cells/ml. Production may be carried out in various types of equipment: shake flask placed in a Kühner Lab-Therm® shaker, Cultibag RM 20/50® (Sartorius), Cell-Ready® (Merck Millipore), BioBundle® (Applikon) and other equivalent equipment, of the same or larger scale. The cells are grown for at least 5 days, up to a maximum of 10 days, depending on culture conditions. Each day, production parameters, cell concentration and cell viability are monitored. During production, components such as amino acids, vitamins, glucose or any other element advantageous for the production process or for the cells may be added. In this case, it is a "fed-batch" or "semicontinuous" culture, which makes it possible to grow cells for a maximum of 21 days. A "batch" or "discontinuous" culture is one in which no compound is added during growth.

Example 4

Isolation of the Fusion Protein Using Affinity Chromatography

The cells and cell debris present in the medium containing the polypeptide according to the invention are removed by centrifugation or depth filtration (Merck Millipore POD Millistak+® or any other equivalent medium) or tangential flow filtration on a membrane having a 0.2 μm cutoff. The supernatant thus obtained is purified by affinity chromatography on a column chelated with a metal such as nickel, cobalt, zinc or copper. In order to promote the bonding of the polypeptide according to the invention, buffer containing 0 to 50 mM imidazol, 0 to 500 mM NaCl, 5 to 20 mM $Na_2HPO_4.2H_2O$ and 5 to 20 mM $NaH_2PO_4.H_2O$ is added to the supernatant and pH is adjusted to between 7 and 8. The polypeptide according to the invention is eluted by gradient using a mixture of two buffers (buffer 1: 500 mM imidazol, 500 mM NaCl, 10 mM $Na_2HPO_4.2H_2O$ and 10 mM $NaH_2PO_4.H_2O$; buffer 2: 20 mM imidazol, 500 mM NaCl, 10 mM $Na_2HPO_4.2H_2O$ and 10 mM $NaH_2PO_4.H_2O$), or in an isocratic manner with buffer containing 50 to 500 mM imidazol, 0 to 500 mM NaCl, 5 to 10 mM $Na_2HPO_4.2H_2O$ and 5 to 10 mM $NaH_2PO_4.H_2O$. Optionally, in order to increase the purity of the polypeptide according to the invention, other purification steps of may be added. These may be filtrations, ions-exchange chromatography, affinity chromatography, hydrophobic interaction chromatography, size-exclusion chromatography or any other type of chromatography.

The elution fractions of interest are separated in an electrophoresis gel in native conditions and stained with Coomassie blue, before being combined according to their profile and dialyzed in water or phosphate buffer or any other buffer suitable for preserving the polypeptide according to the invention. The concentration of the polypeptide is determined using the Sircol® kit (TebuBio) according to the manufacturer's instructions, or using the Bradford assay, or using any other test suitable for quantifying the polypeptide of the invention. In a certain embodiment of the invention, the protein extract obtained is pepsin-digested in order to determine whether the polypeptide according to the invention has a triple-helix structure due to the presence, in the sequence of the polypeptide according to the invention, of a 10× repeat of the motif GPP, described as allowing the trimerization of collagen-derived proteins and peptides. In a favored embodiment, pepsin digestion is carried out by incubating the protein extract containing the polypeptide according to the invention for 5-6 hours in a 37° C. water bath in the presence of pepsin in a ratio (protein extract concentration:pepsin concentration) of 20:1. The pepsin is reconstituted in 20 mM sodium acetate buffer adjusted to pH 4 with acetic acid. The protein extract/pepsin mixture must have an acidic pH. The pH is adjusted with acid acetic and verified using pH paper. After digestion, the reaction is quenched with 2 M Tris, pH 11.4, in a volume 1/10 that of the reaction mixture volume, in order to obtain a solution with basic pH. The reaction mixture is then passed or not through a cutoff filter to remove digested fragments, to concentrate and/or to dialyze the sample against any buffer suitable for preserving the polypeptide according to the invention thus digested. Digestion of the fractions is verified by their migration on an electrophoresis gel in native conditions and stained with Coomassie blue.

FIG. 1 presents an electrophoresis profile showing the presence of the polypeptide according to the invention in the pool of the various fractions obtained after purification on an affinity column. The principal band obtained has a molecular weight around 70 kDa. The presence of bands corresponding to proteins with molecular weights of 14, 15, 17, 18, 30, 50, 60, 80, 150, 190, 250 and >250 kDa are also observed. It should be noted that collagen is described as not migrating with the expected molecular mass, here about 50 kDa for the polypeptide of SEQ 2 when in trimer form. Pepsin digestion of the protein extract obtained confirms that the 70 kDa band corresponds to the polypeptide according to the invention structured in the form of a pepsin digestion-resistant triple-helix. The 70 kDa molecular weight may also be explained by the presence of post-translational modifications of the alpha chains of the polypeptide according to the invention.

Example 5

Method for Determining Von Willebrand Factor-Binding Activity by Means of an ELISA Test One of the embodiments of the present invention consists in measuring the von Willebrand factor-binding activity of the polypeptide according to the invention by the so-called ELISA technique, carried out in 96-well plates (Nunc MaxiSorp). To that end, 100 μl of a solution containing the polypeptide at 2 or 10 μg/ml in phosphate buffer or any other suitable buffer is added in each well and incubated at 22° C. for 18 to 20 hours. After three washes with 200 μl of PBS-0.05% Tween, 200 μl of 1% BSA in phosphate buffer solution (Euromedex, 0.45 μm filter) is added in each well and incubated for 2 hours at room temperature (22° C.). After three washes with 200 μl of PBS-0.05% Tween, 100 μl of various concentrations (expressed in IU/dl) of purified von Willebrand factor (Wilfactin, 100 IU/ml, LFB) and/or of patient plasma diluted in phosphate buffer or any other suitable buffer is incubated for 1.5 hours at room temperature (22° C.). After three new washes, 100 μl of a solution containing a primary anti-vWF antibody coupled with horseradish peroxidase (rabbit anti-human vWF/HRP, DAKO) diluted to 1/8000 in phosphate buffer or any other suitable buffer is incubated for 1 hour at 22° C. and then washed 4 times as described above. 125 μl of tetramethylbenzidine solution (TMB, Sigma) as peroxidase substrate is added and then incubation is carried out in the dark for 10 to a maximum of 45 minutes. The reaction is quenched by adding 125 μl of 2 N HCl (Sigma). Absorbance is quickly measured at 450 nm in a spectrophotometer (Wallac Victor 3). A blank is prepared by replacing the purified vWF or plasma with phosphate buffer or any other suitable buffer.

FIG. 2 presents a result obtained by ELISA of the binding of purified von Willebrand factor (Wilfactin, LFB) used at final concentrations of 0, 0.4 and 2 IU/dl to the polypeptides according to the invention corresponding to SEQ 2, to SEQ 3, to type III collagen (BD Biosciences, positive control) and to HCP (host cell proteins, obtained in the same way as the polypeptides according to the invention from non-transfected CHO cells, negative control), containing two (SEQ 2) and one (SEQ 3) von Willebrand factor-recognition motifs, respectively. These various polypeptides are used at concentrations of 10 or 2 μg/ml (FIGS. 2A and 2B). The results show that only the polypeptide according to the invention containing at least two (SEQ 2) von Willebrand factor-recognition motifs is able to bind this factor in a manner equal to the reference type III collagen.

FIG. 3 presents a result obtained by ELISA of the binding of purified von Willebrand factor (Wilfactin, LFB) used at 2 IU/dl to the polypeptide according to invention (SEQ 2) after pepsin digestion or not and obtaining a pure fraction containing the triple-helix form of the polypeptide according to the invention. Von Willebrand factor-binding is measured for a 5 μg/ml concentration of each polypeptide. The results show a large increase in the binding capacity of the polypeptide according to the invention when it is uniquely in triple-helix form. These results indicate that pepsin treatment makes it possible to digest potential protein contaminants that arise from CHO-S cells and that are able to bind to the nickel- or cobalt-based affinity column, and/or to digest polypeptides according to the invention that do not have a triple-helix structure. This result also suggests that it is the triple-helix form that provides the activity of the polypeptide according to the invention.

FIG. 4 presents the binding measurement for various von Willebrand factor concentrations (0, 0.05, 0.1, 0.2, 0.4, 1 and 2 IU/dl) of the polypeptide according to invention (SEQ 2) and of type III collagen coated at 2 μg/ml. It is observed that the polypeptide according to the invention has sensitivity equal to that of type III collagen for low von Willebrand factor concentrations. This point is particularly important because the objective of the test using the polypeptide according to the invention is to determine the activity for very low plasma concentrations of von Willebrand factor, as observed for type 2 patients.

FIG. 5 presents a result obtained by ELISA of the binding of purified von Willebrand factor (Wilfactin, LFB), used at 2 IU/dl, to the polypeptide according to the invention (SEQ 2) and to type III collagen used at concentrations of 2, 1, 0.5, 0.25, 0.125, 0.0625 and 0.03125 μg/ml. The results confirm that the polypeptide according to the invention is able to bind von Willebrand factor in a manner equal to type III collagen used as a reference with the same sensitivity.

Application of the polypeptide according to the invention relates to measuring von Willebrand factor binding-activity present in the plasma of healthy patients or patients with von Willebrand disease. FIG. 6 presents the measurement of plasma von Willebrand factor-binding to the polypeptide according to the invention for various dilutions (1/50, 1/100, 1/200, 1/400 and 1/800) of a reference plasma. These dilutions are those typically used for determining the standard curve obtained from a reference plasma and essential for calculating von Willebrand factor collagen-binding activity for a given patient. The results show the linearity of plasma von Willebrand factor-binding of the polypeptide according to the invention with a linear regression line having a correlation coefficient ($R^2$) equal to 0.9976.

Measuring von Willebrand factor collagen-binding should make it possible to facilitate the classification of patients into the various types of von Willebrand disease. Table I presents the values obtained by ELISA of plasma from type I patients, type II patients or patients suspected of having anti-vWF antibody (mimicking type III) versus healthy patients and the ratio of activity measurement (collagen binding, CB) to antigen measurement (Ag). It is noted that this ratio is superior to 0.7 for type I patients, inferior to 0.7 for type II patients, and that type III patients or patients having anti-vWF antibodies have a virtually non-existent CB % and Ag %, confirming the advantage of the polypeptide according to the invention for classifying these patients. It should be noted that the polypeptide according to the invention distinguishes type I and II patients better than type III collagen (100% correlation with clinical data versus 78%).

TABLE I

Classification of healthy patients and patients with pathology according to their von Willebrand factor CB/Ag ratio (activity measurement (collagen binding, CB)/antigen measurement (Ag)), the measurement being obtained either on the polypeptide having the or some of sequence SEQ 2, or on type III collagen used as a reference (BD Biosciences) coated at 2 μg/ml. The polypeptide of sequence SEQ 2 makes it possible to distinguish type I patients from type II patients with a better correlation to clinical data than with type III collagen (100% versus 78%).

| | Seq 2 | | | | | | Type III collagen | | | | | |
|---|---|---|---|---|---|---|---|---|---|---|---|---|
| Patients | Mean CB % | Ag % | CB/Ag ratio | Interpretation | Classification | Correlation | Mean CB % | Ag % | CB/Ag ratio | Interpretation | Classification | Correlation |
| Patient 1 | 150 | 117 | 1.28 | Normal | Normal | Yes | 164 | 117 | 1.40 | Normal | Normal | Yes |
| Patient 2 | 150 | 86 | 1.74 | Normal | Normal | Yes | 105 | 86 | 1.22 | Normal | Normal | Yes |
| Patient 3 | 59 | 45 | 1.31 | Type 1 | Type 1 | Yes | 37 | 45 | 0.82 | Type 1 | Type 1 | Yes |
| Patient 4 | 22 | 17 | 1.29 | Type 1 | Type 1 | Yes | 24 | 17 | 1.41 | Type 1 | Type 1 | Yes |
| Patient 5 | 33 | 22 | 1.50 | Type 1 | Type 1 | Yes | 17 | 22 | 0.77 | Type 1 | Type 1 | Yes |
| Patient 6 | 11 | 23 | 0.48 | Type 2 | Type 2 | Yes | 17 | 23 | 0.74 | Type 1 | Type 2 | No |
| Patient 7 | 20 | 40 | 0.50 | Type 2 | Type 2 | Yes | 19 | 40 | 0.48 | Type 2 | Type 2 | Yes |
| Patient 8 | 16 | 27 | 0.59 | Type 2 | Type 2 | Yes | 24 | 27 | 0.89 | Type 1 | Type 2 | No |
| Patient 9 | 1 | 5 | 0.20 | vWF activity | vWF activity | Yes | 0 | 5 | 0.00 | vWF activity | vWF activity | Yes |
| Correlation | | | 100.00% | | | | | | 78.0% | | | |

The major advantage of measuring von Willebrand factor collagen-binding (vWF:CB, von Willebrand factor:collagen binding), in contrast with measuring its GpIb-binding after ristocetin activation, lies in the fact that this assay is very sensitive to the loss of high molecular weight multimers, elements that determine von Willebrand factor activity. It thus makes it possible to distinguish type 2 patients and in particular subtypes 2A and 2M.

A recent study showed the advantage using N-acetylcysteine (NAC) in the treatment of thrombotic thrombocytopenic purpura (TTP) resulting from platelet adhesion to very large von Willebrand factor multimers (Chen J et al., *J Clin Invest.* 2011 121(2):593-603). These multimers are the consequence of a deficiency of von Willebrand factor maturation enzyme, ADAMTS13 (a disintegrin and metalloproteinase with a thrombospondin type 1 motif, member 13). Treating a plasma pool with NAC leads to the loss of high molecular weight multimers and is associated with decreased von Willebrand factor collagen-binding.

Example 6

Comparison of the ELISA Test According to the Invention and Two Commercial ELISA Kits (Collagen-Based) in the Context of a Multicenter Clinical Trial As described above, one of the uses of the present invention consists in measuring the von Willebrand factor-binding activity of the polypeptide according to the invention by the so-called ELISA technique. In order to validate this test in comparison with collagen-based ELISA kits already on the market, a multicenter clinical trial (6 centers; authorization 2012/58—RCB ID No. 2012-A01537-36) including 121 patients was carried out. The plasmas collected were from patients distributed as follows:

31 control subjects,
28 patients with type 1 deficiency,
9 patients with type 3 deficiency,
18 patients with type 2A deficiency,
17 patients with type 2B deficiency,
18 patients with type 2M deficiency.

The commercial ELISA kits selected for this trial contain either type I collagen (TECHNOZYM® vWF:CBA ELISA Collagen type I; ref. 5450311; Technoclone GmbH) or type III collagen (ASSERACHROM® vWF:CB; ref. 00239; Stago). The von Willebrand factor-binding activity for these two kits was measured according to the instructions provided by the supplier.

The ELISA test based on the polypeptide according to the invention was carried out at a final concentration of 2 μg/ml of polypeptide having the or some of sequence SEQ 2 and the plasmas diluted to 1/400 were measured following the protocol described above. The standard range used for determining von Willebrand factor-binding activity was obtained from the plasma standard of the ASSERACHROM® vWF:CB kit.

The results presented in table II show the means and standard deviations obtained for each test. A good correlation was observed between the activity values of normal and pathological plasmas obtained with the ELISA test using the polypeptide according to the invention and those obtained with the commercial kits.

TABLE II

Measurement of von Willebrand factor collagen-binding activity for each ELISA according to deficiency type.

| Patients (number) | CBA Stago Type III collagen Mean (SD) | CBA Cryopep Type I collagen Mean (SD) | ELISA Polypeptide SEQ 2 2 μg/ml Mean (SD) |
|---|---|---|---|
| Controls (31) | 103 (22.1) | 161 (40.7) | 98.1 (28.1) |
| Type 1 (28) | 23.9 (8.9) | 22.2 (11.7) | 19.7 (7.5) |
| Type 3 (9) | 1 (0.3) | 0.2 (0.4) | 1.6 (2.1) |
| Type 2A (18) | 15.0 (8.8) | 10.0 (10.8) | 16.9 (11.3) |
| Type 2B (17) | 29.5 (17.1) | 31.4 (26.6) | 31.8 (19.5) |
| Type 2M (18) | 21.8 (13.1) | 15.9 (19.8) | 22.5 (17.7) |

These results strengthen the data concerning the ability of the polypeptide according to the invention to:

bind von Willebrand factor in a manner equal to native collagens,
distinguish patients having a von Willebrand factor deficiency in comparison with controls,
be used in an ELISA test as a replacement for native collagens.

REFERENCES

Patent References

WO2010034718
WO2007052067
EP 1 870 460
EP 2383338

Non-Patent References

Flood V H, J Thromb Haemost. 2012 Apr. 16
Springer T A, J Thromb Haemost. 2011 July; 9 Suppl 1:130-43
Schneppenheim R, Thromb Res. 2011; 128 Suppl 1:S3-7
Chen C and Raghunath M. Fibrogenesis Tissue Repair. 2009 Dec. 15; 2:7
Herr A B and Farndale R W, J Biol Chem. 2009 Jul. 24; 284(30):19781-5
Lisman T et al., Blood. 2006 Dec. 1; 108(12):3753-6
Xu H et al., Matrix Biol. 2011 January; 30(1):16-26
Giudici C et al., J Biol Chem. 2008 Jul. 11; 283(28):19551-60
Brondijk T H et al. Proc Natl Acad Sci USA. 2012 Apr. 3; 109(14):5253-8
Verkleij et al., Blood. 1998 May 15; 91(10):3808-16
Bonnefoy A et al. J Thromb Haemost. 2006 October; 4(10): 2151-61
Favaloro E J, Thromb Haemost. 2010 November; 104(5): 1009-21
Baronciani L et al. J Thromb Haemost. 2006 September; 4(9):2088-90
Heemskerk J W M et al. J Thromb Haemost. 2011 April; 9(4):856-8
Werkmeister J and Ramshaw J. Biomed Mater. 2012 February; 7(1):012002
Chen J et al., J Clin Invest. 2011 121(2):593-603
Needleman and Wunsch, J Mol Biol 1970 48:443

The invention claimed is:

1. A method for diagnosing von Willebrand disease in a patient, comprising the following steps:

a) Providing a polypeptide selected from:

the polypeptide comprising the sequence from position 24 to position 184 of SEQ ID NO: 2, the polypeptide comprising the sequence from position 24 to position 205 of SEQ ID NO: 4, the polypeptide comprising the sequence from position 24 to position 226 of SEQ ID NO: 5, a von Willebrand factor-binding polypeptide comprising the peptide motif $Z_1$-(SEQ ID NO:6)-$Z_2$-(SEQ ID NO:6) and the peptide motif $(GPP)_k$ wherein independently $Z_1$ represents a linker comprising 6 to 12 amino acids, $Z_2$ represents a linker comprising 6 to 12 amino acids, k is an integer between 4 and 15;

b) Contacting a biological sample previously taken from the patient with said polypeptide;

c) Measuring the binding of von Willebrand factor present in the biological sample to the polypeptide of step a) in order to measure von Willebrand factor collagen-binding activity.

2. The method for diagnosing von Willebrand disease in a patient according to claim 1, wherein $Z_1$ and $Z_2$ independently represent a peptide motif of formula $(GAA_1AA_2)_{n1}(GAA_3AA_4)_{n2}(GAA_5AA_6)_{n3}(GAA_7AA_8)_{n4}$ wherein independently $AA_1$, $AA_3$, $AA_5$ and $AA_7$ independently represent amino acids D or A, $AA_2$, $AA_4$, $AA_6$ and $AA_8$ independently represent amino acids A or P, $n_1$, $n_2$, $n_3$ and $n_4$ are independently selected from 0, 1, 2, 3 or 4 and the sum $n_1+n_2+n_3+n_4$ is equal to 2, 3 or 4.

3. The method for diagnosing von Willebrand disease in a patient according to claim 1, characterized in that wherein $Z_1$ and $Z_2$ represent the peptide motif GDAGAPGAP (SEQ ID NO: 7).

4. The method for diagnosing von Willebrand disease according to claim 1, further comprising determining the quantity of von Willebrand factor present in the sample.

5. The method for diagnosing according to claim 1, wherein the polypeptide of step a) is attached to a solid support.

6. The method for diagnosing according to claim 1, wherein steps b) and c) are carried out in flow conditions.

7. A polypeptide characterized in that it is selected from:

the polypeptide comprising the sequence of SEQ ID NO: 2, the polypeptide comprising the sequence from position 24 to position 184 of SEQ ID NO: 2, the polypeptide comprising the sequence of SEQ ID NO: 4, the polypeptide comprising the sequence from position 24 to position 205 of SEQ ID NO: 4, the polypeptide comprising the sequence of SEQ ID NO: 5, the polypeptide comprising the sequence from position 24 to position 226 of SEQ ID NO: 5, and a von Willebrand factor-binding polypeptide comprising the peptide motif $Z_1$-(SEQ ID NO:6)-$Z_2$-(SEQ ID NO:6) and the peptide motif $(GPP)_k$ wherein independently $Z_1$ represents a linker comprising 6 to 12 amino acids, $Z_2$ represents a linker comprising 6 to 12 amino acids, k is an integer between 4 and 15.

8. A kit for determining von Willebrand factor collagen-binding activity, comprising:

a) a polypeptide according to claim 7;

b) a detection reagent for determining von Willebrand factor collagen-binding.

9. The kit according to claim 8, comprising a von Willebrand factor-binding antibody.

* * * * *